United States Patent [19]

Kummer et al.

[11] 4,113,754
[45] Sep. 12, 1978

[54] ISOLATION AND REGENERATION OF RHODIUM-CONTAINING CATALYSTS FROM DISTILLATION RESIDUES OF HYDROFORMYLATION REACTIONS

[75] Inventors: Rudolf Kummer, Frankenthal; Heinz-Walter Schneider; Kurt Schwirten, both of Ludwigshafen, all of Fed. Rep. of Germany

[73] Assignee: BASF Aktiengesellschaft, Ludwigshafen am Rhein, Fed. Rep. of Germany

[21] Appl. No.: 780,297

[22] Filed: Mar. 23, 1977

[30] Foreign Application Priority Data

Apr. 6, 1976 [DE] Fed. Rep. of Germany ....... 2614799

[51] Int. Cl.$^2$ ............................................. C07F 15/00
[52] U.S. Cl. .................................. 260/429 R; 252/415; 252/421; 260/429 BQ; 260/604 HF
[58] Field of Search ..... 260/429 R, 604 HF, 429 BQ; 252/415, 421

[56] References Cited

U.S. PATENT DOCUMENTS

| 3,515,757 | 6/1970 | Sibert | 260/429 R X |
| 3,547,964 | 12/1970 | Olivier | 260/429 R |
| 3,560,539 | 2/1971 | Booth | 260/429 R |
| 3,755,393 | 8/1973 | Kniese et al. | 260/429 R |
| 3,968,134 | 7/1976 | Gregorio et al. | 260/429 R |
| 4,021,463 | 5/1977 | Kummer et al. | 260/429 R |

*Primary Examiner*—Helen M. S. Sneed
*Attorney, Agent, or Firm*—Keil, Thompson & Shurtleff

[57] ABSTRACT

The isolation and regeneration of catalysts of type I or II $$ClRh(CO)(PR_3)_2 \qquad\qquad I$$

$$HRh(CO)(PR_3)_3 \qquad\qquad II,$$

where the R's are identical or different hydrocarbon radicals, to give the catalysts in a pure form, is effected by regenerating aqueous rhodium salt solutions, as obtained on treating distillation residues of hydroformylation mixtures with oxygen-containing mineral acids and peroxides, by a method wherein the said aqueous rhodium salt solutions are treated with a cation exchanger, the latter is then separated from the solution, the absorbed rhodium ions are desorbed with hydrochloric acid, the hexachlororhodate solutions, containing hydrochloric acid, are reacted, in the presence of a water-soluble organic solvent and a tertiary phosphine $PR_3$, with carbon monoxide, or with compounds which eliminate carbon monoxide, at from 0° to 150° C and from 1 to 5 bars, and the resulting complexes I or, if the process is carried out under hydrogenating conditions, the resulting complexes II, are separated off.

10 Claims, No Drawings

ISOLATION AND REGENERATION OF RHODIUM-CONTAINING CATALYSTS FROM DISTILLATION RESIDUES OF HYDROFORMYLATION REACTIONS

The present invention relates to a new process for isolating and regenerating rhodium-containing catalysts from distillation residues obtained from the hydroformylation reaction of olefins with carbon monoxide and hydrogen.

The reaction of olefins with carbon monoxide and hydrogen at elevated temperature and superatmospheric pressure, in the presence of certain catalytic metal carbonyl complexes, to give aldehydes, has been disclosed.

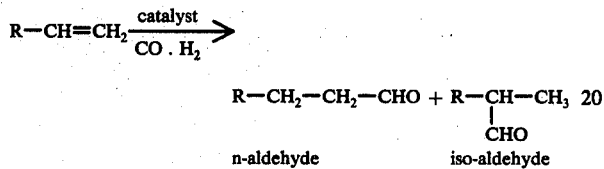

In these equations, R is an organic radical.

If cobalt-containing catalysts are used for this reaction, as is frequently the case, the reaction temperatures required are relatively high, and this favors the formation of the iso-aldehydes, which as a rule are undesired products. It is true that rhodium-containing catalysts permit the use of substantially milder reaction conditions so that a higher proportion of n-aldehydes is produced (cf. Catalysis Reviews, 6 (1972), 68), but hitherto these catalysts have only found hesitant acceptance in industrial hydroformylation practice, because the recovery and regeneration of the expensive noble metal presents substantial difficulties.

Both in batch and in continuous operation, the more volatile constituents of the reaction mixture, including the process products, are separated off by distillation, whilst the catalysts accumulate in the higher-boiling distillation residue. It is true that this catalyst-containing residue can be recycled to the hydroformylation, but ultimately not all of it can be recycled because the amount of residue progressively increases and because the activity of the catalyst progressively decreases.

The recovery and regeneration of the expensive rhodium catalysts are therefore of vital economic importance but the conventional processes for this purpose have proved rather unsatisfactory. Both in the process of German Laid-Open Application No. 2,262,885 (decomposition of the catalysts with steam at an elevated temperature) and in the process of German Published Application No. 1,954,815 (adsorption of rhodium on basic ion exchangers) the noble metal is obtained in the elementary form, which can only be reconverted to the active complex by a very laborious procedure.

According to the process of U.S. Pat. No. 3,547,964, the catalyst-containing distillation residue is treated with aqueous acids and peroxides, the aqueous phase containing noble metal salts is separated off, the excess peroxide is destroyed by heating and the aqueous solution is reacted with carbon monoxide under pressure in the presence of an inert, water-immiscible solvent and a complex-forming component, for example triphenylphosphine. This gives an organic solution of a noble metal carbonyl complex which can be recycled to the hydroformylation reaction. However, even this process has disadvantages, since the regeneration of the catalyst is carried out under pressure in a system of two liquid phases and therefore does not take place rapidly enough and in particular does not take place sufficiently quantitatively. Furthermore, the conventional method only permits the manufacture of solutions in which the catalyst merely consists of the central noble metal atom and the zero-valent ligands CO and L, L being, for example, a tertiary phosphine. Frequently, however, complexes in which one L is replaced by halogen are preferred, for reasons of stability.

It is an object of the present invention to isolate the rhodium from the distillation residues obtained from the hydroformylation reaction and reconvert them quantitatively, in a simple manner, to an active form.

It is a further object of the invention to recover catalysts of type I or II

where the R's are identical or different hydrocarbon radicals, from the distillation residues.

According to the proposal of U.S. patent application Ser. No. 616,448, these objects are achieved by reacting aqueous rhodium salt solutions, which are obtained on treating distillation residues of hydroformylation mixtures with acids and peroxides and then destroying the peroxides, in the presence of a water-soluble organic solvent, of hydrohalic acids or alkali metal halides, and of tertiary phosphines $PR_3$, with carbon monoxide or compounds which eliminate carbon monoxide, at from 0° to 150° C. and from 1 to 250 bars, and isolating the compounds I which hereupon precipitate or, if the last process stage is carried out under hydrogenating conditions, isolating the compounds II, which also precipitate.

We have found that this method can be improved by providing a process for isolating and regenerating catalysts of type I or II

where the R's are identical or different optionally halogen- or oxygen-substituted hydrocarbon radicals, in a pure form, by regenerating aqueous rhodium salt solutions, as obtained on treating distillation residues of hydroformylation mixtures with oxygen-containing mineral acids and peroxides, wherein the said aqueous rhodium salt solutions are treated with a cation exchanger, the latter is then separated from the solution, the absorbed rhodium ions are desorbed with hydrochloric acid, the hexachlororhodate solutions, containing hydrochloric acid, are reacted, in the presence of a water-soluble organic solvent and a tertiary phosphine $PR_3$, with carbon monoxide, or with compounds which eliminate carbon monoxide, at from 0° to 150° C. and from 1 to 5 bars, and the resulting complexes I or, if the process is carried out under hydrogenating conditions, the resulting complexes II, are separated off.

The distillation residues obtained from the hydroformylation reaction using rhodium catalysts consist essentially of heavy aldehydes, alcohols, aldols, carboxylic acids and esters and as a rule contain from 0.001 to 1% of the noble metal.

Advantageously, 100 parts by weight of such a residue are reacted with from 10 to 1,000 parts by weight of an aqueous oxygen-containing mineral acid of from 1 to 20% strength and with from 10 to 100 parts by weight of a peroxide at from 20° to 120° C., with vigorous stirring.

A suitable oxygen-containing mineral acid is, above all, nitric acid, but sulfuric acid or phosphoric acid may also be used. Hydrohalic acids are unsuitable, above all at fairly high concentration, because they form chlororhodates which are not absorbed by the cation exchangers to be used according to the invention. Suitable peroxides are those which decompose on heating, i.e. above all hydrogen peroxide, but also alkali metal peroxides or persulfates and persulfuric acids. Organic peroxides, e.g. benzoyl peroxide, may also be used.

On oxidative treatment of the hydroformylation residues, the rhodium passes virtually quantitatively into the aqueous phase as $Rh^{+++}$. It is an advantage of the present process that any excess peroxide present does not have to be destroyed before the aqueous solution is subjected to the next process step, i.e. to the treatment with the cation exchanger.

Suitable cation exchangers are, above all, polymers bearing sulfonic acid groups or carboxyl groups, e.g. sulfonated or carboxylated styrene-divinylbenzene resins.

These and similar cation exchangers are commercially available, for example under the tradenames Amberlite ® and Lewatit ®.

The amount of cation exchanger is advantageously chosen so as to provide from 10 to 100 equivalents of acid per gram atom of $Rh^{+++}$. Since the strength of the aqueous $Rh^{+++}$ solutions obtained from the process is from about 0.01 to 0.5% by weight, this means in practice that from about 10 to 1,000 g of the cation exchanger are used per liter of such a solution. The treatment with the cation exchanger is preferably carried out at room temperature, by stirring the aqueous solution with the exchanger for from 30 to 120 minutes, or by passing the solution over an exchanger column so as to provide corresponding residence times. The solution which is left, which may still contain peroxides but is rhodium-free or — which frequently suffices — is substantially rhodium-free, may be used for treating further hydroformulation residues. A particularly advantageous embodiment of the process according to the invention is therefore to treat the hydroformylation residues in portions with a limited volume of aqueous phase and in each case to supplement the peroxide and acid in the recovered solutions only by the amount corresponding to the consumption in the oxidation reaction. To carry out the desorption, the cation exchanger is preferably reacted with from 1N to 5N hydrochloric acid in an amount corresponding to from 20 to 100 moles per gram atom of rhodium.

In the next process stage, the rhodium, present in the form of $[RhCl_6]^{---}$ anions is reacted with phosphines $PR_3$ and carbon monoxide in the presence of water-soluble solvents in the aqueous hydrochloric acid phase, to give the complexes I or, if the process is also being carried out under hydrogenating conditions, to give the complexes II.

Based on rhodium, the amount of phosphine is at least that which corresponds stoichiometrically to formula I or II, but it is advantageous to add up to 100-fold molar excess of phosphine.

The function of the water-soluble organic solvent is to keep the free phosphine in solution in the aqueous-organic phase. The amount of solvent accordingly depends on the amount of the aqueous hydrochloric acid solution, on the nature of the solvent, on the nature and amount of the phosphine and, to a certain degree, also on the nature and amount of the other constituents, resulting from the pretreatment, present in the aqueous phase. This amount varies from case to case but can readily be determined by a few preliminary experiments on model solutions free from noble metal. It is advantageous not to exceed the required minimum amount substantially, but our observations to date have shown that the success of the process according to the invention is not affected even if the proportion of water in the total system is only 10 percent by weight.

Examples of suitable water-soluble organic solvents are acetone, tetrahydrofuran and dioxane and, above all, alcohols of 1 to 4 carbon atoms, e.g. methanol, ethanol, propanol, isopropanol, n-butan-1-ol, n-butan-2-ol, iso-butan-1-ol and iso-butan-2ol. It is advantageous to dissolve the phosphine in the solvent and add it in this form to the aqueous hexachlororhodate solution.

The choice of the phosphine $PR_3$ depends on the nature of the hydroformylation reaction in which the rhodium catalyst is to be used. Preferably, catalysts of type I or II in which the organic radicals of the phosphine are identical or different alkyl, aralkyl, aryl or alkylaryl radicals, each of up to 12 carbon atoms, are used, the total number of carbon atoms in the phosphine being from 12 to 36. All these phosphines, the hydrocarbon radicals of which may also carry halogen substituents or be interrupted by oxygen, have the property essential to the present catalyst regeneration process that they are adequately soluble even in a homogeneous aqueous organic medium but that they form, with rhodium and carbon monoxide, halo-complexes or hydrido-complexes which are only very sparingly soluble in the medium. To this degree, the chemical nature of the phosphines is of lesser importance, so that the proviso that preferably trialkylphosphines or triarylphosphines of 12 to 24 carbon atoms or, above all, triphenylphosphine, should be used merely expresses the fact that these phosphines have hitherto found particularly wide acceptance as rhodium ligands in hydroformylation technology.

If the phosphines are very sparingly soluble in the aqueous organic medium, the presence of a dispersing agent may be of advantage. In that case, fine dispersions are obtained in place of homogeneous solutions, but these dispersions behave like solutions.

In some cases it may be advantageous to heat the aqueous-organic solution prior to the carbonylation, in order to provide the phosphine with the opportunity of forming an adduct with the noble metal.

Carbon monoxide is then passed into the aqueous-organic solution, containing the rhodium-chlorine-phosphine complex and the phosphine, at from 0° to 150° C and from 1 to 5 bars, preferably somewhat below the boiling point of the solution, and at atmospheric pressure. Hereupon, the complexes I precipitate virtually quantitatively, at times together with some of the excess phosphine. Instead of carbon monoxide, compounds which eliminate CO, e.g. formaldehyde, may also be used.

If the carbonylation is carried out under hydrogenating conditions, the hydrido-complexes II, which are also insoluble, are obtained. For this purpose, the reaction is either carried out in the presence of reducing agents which yield hydride ions, e.g. sodium borohydride, at from 0° to 100° C. under atmospheric pressure, or under hydrogen at from 0° to 150° C. and from 1 to 300 bars.

The chloro-complexes I can also be subsequently converted to the hydrido-complexes II by dissolving them in water-soluble organic solvents, hydrogenating them and precipitating the hydrido-complexes by adding water.

The catalysts I or II recovered and regenerated in accordance with the process of the invention, which account for from 95 to 100% of the rhodium content of the starting material, are recycled to the hydroformylation, for example by introducing them into the distillation residue circuit.

The process permits economical use of the industrially important rhodium-catalyzed hydroformylation method. The process can readily be fitted into industrial syntheses and above all permits recovery of the catalysts in the form of the particularly important chloro-complexes I and hydrido-complexes II. A particular advantage of the process is that it can be employed successfully even in cases where rhodium recovery is particularly difficult. Such difficult cases have hitherto been encountered wherever, in continuous operation, the hydroformylation residues have been recycled to the hydroformylation reaction for longer than about 1 week. In such cases, the losses of rhodium, on working-up, rise to about 50%, for reasons which are not fully understood. In contrast, the process of the invention permits recycling of the residue for several months, with virtually no losses of rhodium.

The process is useful, for example, for the manufacture of predominantly normal aldehydes from monoolefins, e.g. propionaldehyde from ethylene, n-butyraldehyde from propylene and n-nonanal from octene, and also, in particular, for the bishydroformylation of conjugated unsaturated compounds with olefinic double bonds, e.g. butadiene, this being a reaction which cannot be carried out economically with conventional cobalt catalysts.

EXAMPLE 1,000 g of the distillation residue which had formed in the course of 8 months in the continuous hydroformylation of propylene to give, predominantly, n-butyraldehyde, and which contained 340 mg of rhodium, predominantly in the form of the complex HRh(CO)(PR$_3$)$_3$ (R = phenyl), were stirred with 1,000 g of 1 N nitric acid and 300 g of 50% strength hydrogen peroxide, first for 20 hours at room temperature and then for a further 4 hours at from 40° to 60° C. This caused about 98% of the rhodium to pass into the aqueous acid phase which was then charged, in the course of 60 minutes, onto a column containing 250 g of a cation exchanger with sulfo groups (Amberlite ® JR 120; 1.9 mole equivalents of acid per l). The rhodium-free solution which remained was concentrated slightly, brought back to the initial amount and initial concentration with nitric acid and hydrogen peroxide, and used for the treatment of a further 1,000 g of distillation residue. After a total of 10 cycles of this type, that is to say after working-up 10 kg of residue, about 3.4 g of rhodium had accumulated in the cation exchanger. The rhodium was then eluted with 1,000 ml of 3N hydrochloric acid, after which the solution was concentrated to 300 ml, mixed with 600 ml of iso-propanol and 26.5 g of triphenylphosphine, and treated with carbon monoxide in the course of 15 minutes at 100° C. under atmospheric pressure. After the mixture had cooled, the yellow crystals of Rh(CO)(PR$_3$)$_2$Cl (R = phenyl) were separated off. The yield of recovered rhodium, based on all the process stages, was 97%.

Reduction of the chloro complex, in isopropanol/water, by means of sodium boranate in the presence of additional triphenylphosphine gave a quantitative yield of the corresponding hydrido complex.

We claim:

1. A process for isolating and regenerating a catalyst of type I $$ClRh(CO)(PR_3)_2 \qquad I$$

wherein the R 's are identical or different optionally halogen- or oxygen-substituted hydrocarbon radicals, in a pure form, by regenerating an aqueous rhodium salt solution as obtained on treating a distillation residue of a rhodium-catalyzed hydroformylation reaction product mixture with an oxygen-containing mineral acid and a peroxide, wherein the said aqueous rhodium salt solution is treated with a cation exchanger, the latter is then separated from the solution, the absorbed rhodium ions are desorbed with hydrochloric acid, the hexachlororhodate solution containing hydrochloric acid is reacted in the presence of a water-soluble organic solvent and a tertiary phosphine PR$_3$ and at from 0° to 150° C. and from 1 to 5 bars with carbon monoxide or with a compound which eliminates carbon monoxide, and the resulting complex I, is separated off.

2. A process as claimed in claim 1, wherein the cation exchanger is employed in an amount to provide 10 to 100 equivalents of acid per gram atom of Rh$^{+++}$ in the aqueous rhodium salt solution.

3. A process as claimed in claim 1, wherein the cation exchanger is a sulfonated or carboxylated styrene-divinylbenzene resin.

4. A process as claimed in claim 1, wherein the adsorbed rhodium ions are desorbed by reaction with 1N to 5N hydrochloric acid in an amount of from 20 to 100 moles per gram atom of rhodium.

5. A process for isolating and regenerating a catalyst of type II $$HRh(CO)(PR_3)_3 \qquad II,$$

where the R's are identical or different optionally halogen- or oxygen-substituted hydrocarbon radicals, in a pure form, by regenerating an aqueous rhodium salt solution as obtained on treating a distillation residue of a rhodium-catalyzed hydroformylation reaction product mixture with an oxygen-containing mineral acid and a peroxide, wherein the said aqueous rhodium salt solution is treated with a cation exchanger, the latter is then separated from the solution, the abosorbed rhodium ions are desorbed with hydrochloric acid, the hexachlorrhodate solution containing hydrochloric acid is reacted in the presence of a water-soluble organic solvent and a tertiary phosphine PR$_3$ at from 0° to 150° C and from 1 to 5 bars with carbon monoxide or with a compound which eliminates carbon monoxide, using under hydrogenation conditions hydrogen or hydride ions to form the complex II, and the resulting complex II is separated off.

6. A process as claimed in claim 5, wherein the cation exchanger is employed in an amount to provide 10 to 100 equivalents of acid per gram atom of $Rh^{+++}$ in the aqueous rhodium salt solution.

7. A process as claimed in claim 5, wherein the cation exchanger is a sulfonated or carboxylated styrene-divinylbenzene resin.

8. A process as claimed in claim 5, wherein the absorbed rhodium ions are desorbed by reaction with 1N to 5N hydrochloric acid in an amount of from 20 to 100 moles per gram atom of rhodium.

9. A process as claimed in claim 5 wherein said hydrogenating conditions are provided by using hydrogen at 0° to 150° C. and a pressure of 1 to 300 bars.

10. A process as claimed in claim 5 wherein said hydrogenating conditions are provided by using a reducing agent which yields hydride ions used at a temperature of from 0° to 100° C. and at atmospheric pressure.

* * * * *